United States Patent [19]
Bargiotti et al.

[11] Patent Number: 5,532,218
[45] Date of Patent: Jul. 2, 1996

[54] 3'-AZIRIDINO-ANTHRACYCLINE DERIVATIVES

[75] Inventors: Alberto Bargiotti; Michele Caruso; Maria Grandi; Marina Ripamonti; Antonino Suarato, all of Milan, Italy

[73] Assignee: Farmitalia Carlo Erba S.R.L., Milan, Italy

[21] Appl. No.: 345,450

[22] Filed: Nov. 21, 1994

[30]     Foreign Application Priority Data

Dec. 13, 1993 [GB] United Kingdom ............ 9325417

[51] Int. Cl.⁶ .................... A61K 31/70; C07H 15/24
[52] U.S. Cl. ............................ 514/34; 536/6.4
[58] Field of Search ................ 536/6.4; 514/34

[56]                References Cited
           U.S. PATENT DOCUMENTS 5,413,992  5/1995  Nicolaou et al. ............ 536/6.4

*Primary Examiner*—Elli Peselev
*Attorney, Agent, or Firm*—Oblon, Spivak, McClelland, Maier & Neustadt

[57]               ABSTRACT

Anthracycline glycosides of general formula 1 and 2:

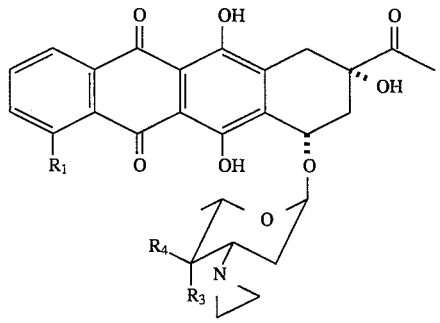

-continued

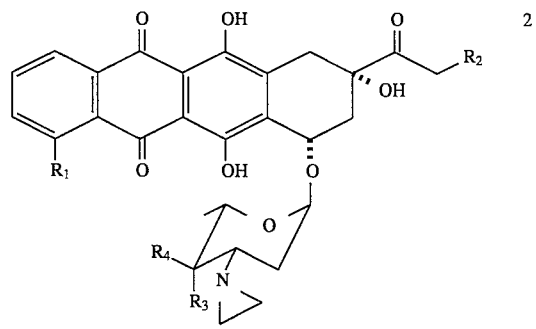

wherein $R_1$ is hydrogen or a methoxy group; $R_2$ is hydrogen, a hydroxy group or represents an acyloxy residue of formula 3 —O—$COR_5$ wherein $R_5$ is a linear or branched $C_1$–$C_8$ alkyl, an aryl group or a heterocyclic mono or bicyclic ring, each of which may be unsubstituted or substituted with (a) an amino group $NR_6R_7$ in which $R_6$ and $R_7$ are independently hydrogen or $C_1$–$C_4$ alkyl or (b) a carboxy group; $R_3$ and $R_4$ both represent hydrogen or one of $R_3$ and $R_4$ is hydrogen and the other is hydroxy group or a group of formula —$OSO_2R_8$ in which $R_8$ may be a linear or branched alkyl group containing from 1 to 6 carbon atoms or an aryl group unsubstituted or substituted by 1 to 3 substituents each of which may independently be a linear or branched alkyl or alkoxy group of from 1 to 6 carbon atoms, a halogen atom or a nitro group; and pharmaceutically acceptable salts thereof; are active as antitumor agents.

10 Claims, No Drawings

3'-AZIRIDINO-ANTHRACYCLINE DERIVATIVES

The invention relates to novel anthracycline glycosides endowed with antitumor activity, to processes for their preparation and to pharmaceutical compositions containing them.

The invention provides anthracycline glycosides, related to daunorubicin and doxorubicin, in which the 3'-amino group of the sugar residue is enclosed in an aziridino ring and, optionally, the hydroxy group at C-4' of the sugar may be protected in the form of a sulphonate. The invention also provides water soluble derivatives and pharmaceutically acceptable acid addition salts thereof.

The present invention provides a compound which is an anthracycline glycoside of formula 1 or 2:

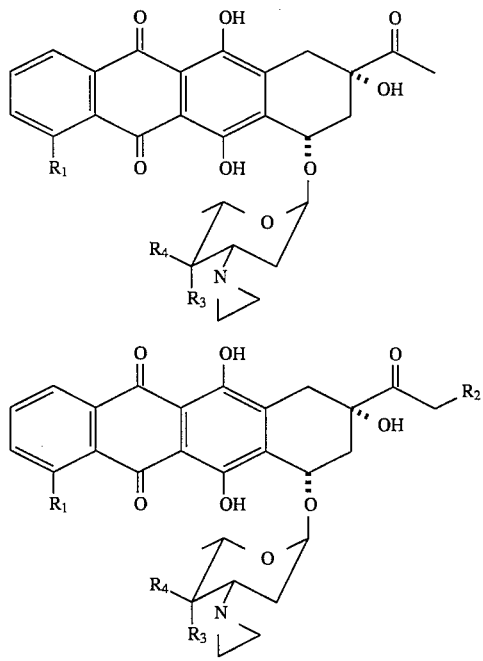

wherein $R_1$ is hydrogen or methoxy group; $R_2$ is hydrogen, a hydroxy group or represents an acyloxy residue of formula 3:

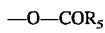

—O—COR$_5$   3 wherein $R_5$ is a linear or branched $C_1$–$C_8$ alkyl, a mono or bicyclic aryl, preferably phenyl, or a hetero mono or bicyclic ring, preferably pyridyl, each of which groups may optionally be substituted with (a) an aminogroup —NR$_6$R$_7$ in which $R_6$ and $R_7$ are independently hydrogen or $C_1$–$C_4$ alkyl or (b), a carboxy group; $R_3$ and $R_4$ both represent hydrogen or one of $R_3$ and $R_4$ is hydrogen and the other is a hydroxy group or a group of formula —OSO$_2$R$_8$ in which $R_8$ may be a linear or branched alkyl group containing from 1 to 6 carbon atoms, for example 1 to 4 carbon atoms; $R_8$ may in particular be methyl, ethyl, n-propyl or isopropyl.

Alternatively, $R_8$ may be an aryl group such as phenyl, unsubstituted or substituted by 1 to 3 substituents each of which may independently be a linear or branched alkyl or alkoxy group of from 1 to 6 carbon atoms for example from 1 to 3 carbon atoms, a halogen atom or a nitro group. Examples of halogen atoms include fluorine, chlorine, bromine and iodine, preferably fluorine or chlorine, more preferably chlorine.

In the present invention, an aryl group is a monocyclic or bicyclic aromatic hydrocarbon of 6 to 10 carbon atoms, for example phenyl or naphtyl. A heterocyclic ring is a 5- or 6-membered saturated or unsaturated heterocyclyl ring, containing at least one hetero atom selected from O, S and N, which is optionally fused to a second 5- or 6-membered, saturated or unsaturated heterocyclyl group.

Examples of saturated and unsaturated heterocyclic rings include pyrazolyl, imidazolyl, pyridyl, pyrazyl, pirimidyl, pyridazynyl, morpholino, thiomorpholino, furyl and thienyl rings.

Preferably $R_2$ is hydroxy or O-nicotinyl, $R_3$ is hydroxy or —OSO$_2$R$_8$ where $R_8$ is $C_1$–$C_4$ alkyl, and $R_4$ is hydrogen.

Examples of compounds of the invention include:

(1a) 3'-deamino-3'-[1-aziridinyl]-4-O-methansulfonyl daunorubicin ($R_1$=OCH$_3$, $R_4$=H, $R_3$=OSO$_2$CH$_3$)

(1b) 4-demethoxy-3'-deamino-3'-[1-aziridinyl]-4'-O-methansulfonyl daunorubicin ($R_1$=$R_4$=H, $R_3$=OSO$_2$CH$_3$)

(1c) 3'-deamino-3'-[1-aziridinyl]-daunorubicin ($R_1$=OCH$_3$, $R_4$=H, $R_3$=OH)

(1d) 4-demethoxy-3'-deamino-3'-[1-aziridinyl]-daunorubicin ($R_1$=$R_4$=H, $R_3$=OH)

(2a) 3'-deamino-3'-[1-aziridinyl]-4'-O-methansulfonyl-14-nicotinate-doxorubicin ($R_1$=OCH$_3$, $R_2$=O-nicotinoyl, $R_4$=H, $R_3$=OSO$_2$CH$_3$)

(2b) 3'-deamino-3'-[1-aziridinyl]-14-nicotinate-doxorubicin ($R_1$=OCH$_3$, $R_2$=O-nicotinoyl, $R_4$=H, $R_3$=OH)

(2c) 3'-deamino-3'-[1-aziridinyl]-4'-O-methansulfonyl doxorubicin ($R_1$=OCH$_3$, $R_2$=OH, $R_4$=H, $R_3$=OSO$_2$CH$_3$)

(2d) 4-demethoxy-3'-deamino-3'-[1-aziridinyl]-4'-O-methansulfonyl doxorubicin ($R_1$=$R_4$=H, $R_2$=OH, $R_3$=OSO$_2$CH$_3$)

(2e) 3'-deamino-3'-[1-aziridinyl]-doxorubicin ($R_1$=OCH$_3$, $R_4$=H, $R_2$=$R_3$=OH)

(2f) 4-demethoxy-3'-deamino-3'-[1-aziridinyl]-doxorubicin ($R_1$=$R_4$=H, $R_2$=$R_3$=OH)

(2g) 3'-deamino-3'-[1-aziridinyl]-4'-iododoxorubicin ($R_1$=OCH$_3$, $R_2$=OH, $R_4$=H, $R_3$=I)

(2h) 3'-deamino-3'-[1-aziridinyl]-4'-deoxydoxorubicin ($R_1$=OCH$_3$, $R_2$=OH, $R_3$=$R_4$=H)

and pharmaceutically acceptable salts thereof such as hydrochloride salts.

Further, the present invention provides a process for the preparation of an aziridino anthracycline glycoside of formula 1 or 2 as above defined or pharmaceutically acceptable salt thereof, which process comprises:

(a) converting an anthracycline of general formula 4:

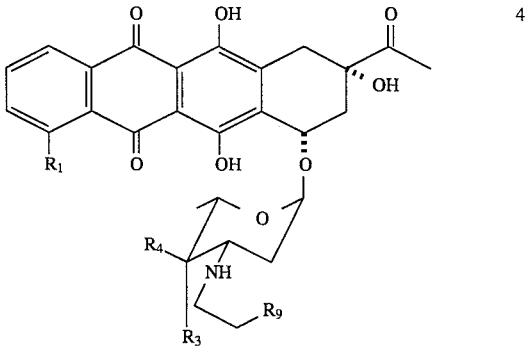

wherein $R_1$, $R_3$ and $R_4$ are as defined above and $R_9$ represents a sulfonate group or halogen atom, preferably a chlorine atom, into an anthracycline of formula 1, the compound of formula 4 preferably being dissolved in an anhydrous organic solvent in the presence of an anhydrous alkali metal salt and a mild base; and, if desired, (b) hydrolizing a derivative of formula 5

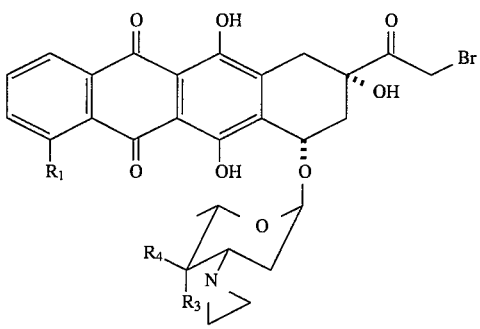

in which $R_1$, $R_3$, $R_4$ are as defined above (which may be prepared from a compound of formula 1 following the procedure as described in U.S. Pat. No. 3,803,124) to obtain an aziridino anthracycline derivative of formula 2 in which $R_2$ is a hydroxy group; and, if desired, (c) reacting a compound of formula 5 as defined above with a salt derivative of formula 3'

$$X^+\text{-}OCOR_5 \qquad 3'$$

in which $R_5$ has the same meaning as above, with the proviso that $R_5$ does not represent a residue bearing a primary amino group, and $X^+$ represents an ion, preferably a sodium or potassium ion, and, if desired, converting the compound of formula 2 thus obtained into a pharmaceutically acceptable salt thereof; or (d) reacting a compound of formula 5 as above defined with a salt derivative of formula 3' in which $R_5$ is a primary amino group masked with an acid sensitive protecting group, then deblocking the protecting group and, if desired, converting the compound of formula 2 thus obtained into a pharmaceutically acceptable salt thereof.

The present invention provides another process for the preparation of an aziridino anthracycline glycoside of formula 2 as above defined or a pharmaceutically acceptable salt thereof, which process comprises:

(a) treating an anthracycline of general fomula 6

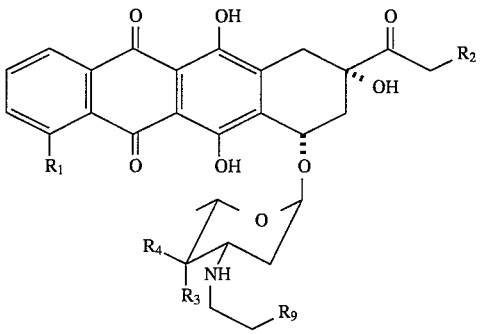

wherein $R_1$, $R_2$, $R_3$, $R_4$ and $R_9$ are as defined above [such compounds have also been disclosed in WO 93/01201], with silica gel and, if desired, converting the compound of formula 2 thus obtained into a pharmaceutically acceptable salt thereof.

It is of note that anthracyclines of formula 4 or 6 are also capable of forming the aziridino ring when treated with silica gel. Mild conditions may be used for this treatment which allows the preparation of compounds of formula 2 starting from basic sensitive ester derivatives such as those of formula 6.

According to the present invention, preferably the reaction conditions for preparing aziridino anthracyclines of formula 1 comprise dissolving a compound of formula 4, as previously defined, in an anhydrous organic solvent, such as anhydrous methylene chloride, in the presence of an anhydrous alkali salt, for example anhydrous sodium or potassium carbonate or hydrogen carbonate, with stirring at a temperature of from 0° to 30° C., preferably at room temperature, and for from 15 minutes to two hours, preferably for about 30 minutes.

In another process, compounds of formula 4 are dissolved in a mixture of organic solvents, such as dry methylene chloride and methanol from 1:1 to 1:3 by volume, then the solution is treated with silica gel, preferably 230–400 mesh, with stirring at a temperature of from 0° C. to 30° C., preferably at room temperature, and for from 15 minutes to two hours, preferably for about 30 minutes.

In a similar process, reaction conditions for transforming compounds of formula 6, as defined above, into aziridino anthracyclines of formula 2 preferably comprise dissolving compounds of formula 6 in an anhydrous organic solvent, such as dry methylene chloride and methanol, and treating the resultant solution with silica gel, preferably 230–400 mesh, with stirring at a temperature of from 0° to 30° C., preferably at room temperature for from 15 minutes to two hours, preferably for about 30 minutes.

The use of a polar solvent, such as methanol, in the silica gel procedure is used in order to remove the anthracycline from the silica.

In another process for the preparation of an aziridino anthracycline glycoside of formula 2 or a pharmaceutically acceptable salt thereof, wherein $R_2$ is a group of formula 3 in which $R_5$ does not represent a residue bearing a primary amino group, preferable reaction conditions comprise reacting a compound of formula 5 with an acid salt derivative of formula 3' as previously defined, in anhydrous polar solvent, preferably acetone or dimethylformamide, at a temperature of from 20° to 60° C., preferably at room temperature, for from 4 to 15 hours, preferably 5 to 12 hours.

Reaction conditions for preparing an aziridino anthracycline glycoside of general formula 2, wherein $R_2$ represents a group of formula 3 in which $R_5$ is a primary amino group, comprises reacting compounds of formula 5, as defined above, with an acid salt derivative of formula 3' in which the amino group is protected with an acid sensitive group, for example the amino group is protected with Schiff's base, in a polar aprotic solvent such as acetone or dimethylformamide, at a temperature of from 20° to 60° C., preferably at room temperature, for from 4 to 15 hours, preferably 5 to 12 hours, then the resultant (N-protected)-ester derivative is deblocked by dissolving it in e.g. methylene chloride and adding distilled water and aqueous hydrochloric acid preferably about the same volume of water as methylene chloride and hydrochloric acid in an amount which corresponds to approximately three equivalents of 0.1N HCl. The mixture is stirred vigorously at a temperature of from 0° to 20° C., preferably at about 15° C., for from 30 minutes to two hours, preferably 45 to 90 minutes, separated and the aqueous phase is dry frozen to obtain the soluble ammonium hydrochloride salt of a C-15 ester derivative of formula 2. Preferably, the primary amino group is protected with a methylenediphenyl group.

As a further aspect, the invention provides pharmaceutical compositions comprising an anthracycline glycoside of formula 1 or 2 or a pharmaceutically acceptable salt thereof in combination with a pharmaceutically acceptable diluent or carrier.

Conventional carriers and diluents may be used. The compositions may be formulated and administered in a conventional manner.

Suitable routes of administration include parenteral administration. For parenteral administration a liquid formulation may be prepared using the active compound and a sterile diluent or carrier which may either dissolve the active compound or provide a suspension for it. The parenteral formulation may be prepared in the form of a sterile solid for reconstitution prior to administration with a suitable vehicle such as physiological saline, sterile water or other sterile vehicle.

The compounds of the invention are useful in methods of treatment of the human and animal body by therapy. They are useful as anti-tumor agents in particular in the treatment of leukaemia or colon adenocarcinoma. A therapeutically effective amount is administered to a patient having a tumor to ameliorate or improve the condition of the patient. An amount sufficient to inhibit the growth of the tumor may be administered.

The dosage to be given can be ascertained using known dosage ranges for doxorubicin and daunorubicin modified by reference to the activity shown by the present compounds in vitro and in vivo anti-tumor tests. Suitable dosages are generally in the range of 1 to 200 mg/m² body surface, preferably from 1 to 100 mg/m², depending on the nature and severity of the disease being treated and on the general condition of the patient.

The following examples illustrate the invention.

EXAMPLE 1

Preparation of
3'-deamino-3'-[1-aziridinyl]-4'-O-methansulfonyl daunorubicin ($R_1$=OCH$_3$, $R_4$=H, $R_3$=OSO$_2$CH$_3$)

3'-N-(2-chloroethyl)-4'-O-methanesulfonyl-daunorubicin (4a, $R_1$=OCH$_3$, $R_4$=H, $R_3$=OSO$_2$CH$_3$, $R_9$=Cl) (0.33 g, 0.05 mmol), prepared as described in WO/ 93/012001 was dissolved in a mixture of anhydrous methylene chloride (10 ml) and methanol (20 ml) and stirred with silica gel (Merck, 200–400 mesh, 2g) at room temperature for 30 minutes. The solution was then filtered, concentrated to dryness and the crude material flash chromatographed on a silica gel column using a mixture of methylene chloride and methanol (95:5 by volume) as the eluting system to give the title compound 1a (yield 0,22 g).

TLC on Kieselgel Plates F254 (Merck), using the eluting system methylene chloride and methanol (98:2 by volume) Rf=0,65. FD-MS: m/z [M+] 631. 2H-NMR (400 MHz, CDCl$_3$) δ; 1.16, 1.25 (m, 2H, aziridine hydrogens); 1.36 (d, J=6.4Hz, 3H, CH3-5'); 1.52 (m, 1H, H-3'); 1.73 (m, 2H, aziridine hydrogens); 1.80 (m, 1H, H-2'eq); 2.09 (m, 1H, H-2'ax); 2.12 (m, 1H, H-8ax); 2,31 (m, 1H, H-8eq); 2.39 (s, 3H, COCH3); 2.98 (d, J=19.2Hz, 1H, H-10ax); 3.21 (dd, J=1.7, 19.2Hz, 1H, H-10eq); 3.22 (s, 3H, CH$_3$SO$_2$); 4.09 (q, J=6.4Hz, 1H, H-5'); 4.10 (s, 3H, OCH$_3$); 4.44 (s, 1H, OH-9); 4.75 (s, 1H, H-4'); 5.28 (m, 1H, H-7); 5.55 (d, J=3.4Hz, 1H, H-1'); 7.41 (d, J=8.1Hz, 1H, H-3); 7.80 (dd, J=7.7, 8.1Hz, 1H, H-2); 8.05 (d, J=7.7Hz, 1H, H-1); 13.30 (s, 1H, OH-11); 14.00 (s, 1H, OH-6).

EXAMPLE 2

Preparation of 4-demethoxy-3'-deamino-3'-[1-aziridinyl]-4'-O-methansulfonyl daunorubicin (1b: $R_1$=$R_4$=H, $R_3$=OSO$_2$CH$_3$)

4-demethoxy-N-(2-hydroxyethyl)daunorubicin (4b: $R_1$=$R_4$=H, $R_3$=OSO$_2$CH$_3$, R9=OH, 0.3 g, 0.5 mmol) was dissolved in a mixture of methylene chloride (10 ml) and methanol (5 ml) and shaken at room temperature with silica gel (3 g) for 30 minutes. The organic solution was then filtered and the solvent removed under reduced pressure. The residue was flash chromatographed on a silica gel column using a mixture of methylene chloride and methanol (95:5 by volume) as the eluting system to give the title compound 1b (0.18 g). TLC on Kieselgel Plates F254 (Merck), using the eluting system methylene chloride and methanol (20:1 by volume) Rf=0.42. FD-MS: m/z [M+] 601.

EXAMPLE 3

Preparation of 3'-deamino-3'-[1-aziridinyl]-4'-O-methansulfonyl-14-nicotinate-doxorubicin (2a: $R_1$=OCH$_3$, $R_2$=O-nicotinoyl, $R_4$=H, $R_3$=OSO$_2$CH$_3$).

3'-deamino-3'-[1-aziridinyl]-4'-O-methansulfonyl-daunorubicin (1a, 0.63 g, 1 mmole), prepared as described in Example 1, was dissolved in a mixture of anhydrous methanol (6 ml) and dioxane (13 ml), ethyl orthoformate (0.5 ml) was added and then the mixture was treated with a solution of bromine (1 g) in anhydrous methylene chloride (5 ml) at 10° C. for 1.5 hours. The reaction mixture was then precipitated with a mixture of ethyl ether (100 ml) and petroleum ether (50 ml). The precipitate was collected and redissolved in a mixture of acetone (15 ml) and 0.25N aqueous hydrogen bromide (15 ml). The mixture was kept at 30° C. for 20 hours, then extracted with n-butanol (50 ml). The organic solvent was removed under reduced pressure and the residue, dissolved in dry acetone (200 ml) was treated with potassium nicotinate (2g) at reflux for one hour. The solvent was removed under reduced pressure and the crude material was chromatographed on a silica gel column using a mixture of methylene chloride and methanol (95:5 by volume) as the eluting system to give the title compound 2a (0.35 g). m.p. 148°–149° C. with decomposition. TLC on Kieselgel Plate F254 (Merck), using the eluting system methylene chloride and methanol (10:1 by volume). Rf=0.37. FD-MS: m/z [M+] 752.

EXAMPLE 4

Preparation of 3'-deamino-3'-[1-aziridinyl]-4'-O-methansulfonyl doxorubicin (2c: $R_1$=OCH$_3$, $R_2$=OH, $R_4$=H, $R_3$=OSO$_2$CH$_3$)

3'-N-(2-chloroethyl)-4'-methansulfonyldoxorubicin (6a: $R_1$=OCH$_3$, $R_2$=OH, $R_9$=Cl, $R_3$=OSO$_2$CH$_3$, $R_4$=H), prepared as described in GB 9114549, is converted into the title compound 2c as described in Example 1. TLC on Kieselgel Plates F254 (Merck), using the eluting system methylene chloride and acetone (8:2 by volume) Rf=0.35. FD-MS: m/z [M+] 647.

EXAMPLE 5

Preparation of 3'-deamino-3'-[1-aziridinyl]-4'-iododoxorubicin (2g: $R_1$=OCH$_3$, $R_2$=OH, $R_4$=H, $R_3$=I).

3'-N-(2-chloroethyl)-4'-iododoxorubicin (6b: $R_1$=OCH$_3$, $R_2$=OH, $R_9$=Cl, $R_3$=I, $R_4$=H), prepared as described in GB 9114549, is converted into the title compound 2g as described in Example 1. TLC on Kieselgel Plates F254

(Merck), using the eluting system methylene chloride and acetone (9:1 by volume) Rf=0.45. FD-MS: m/z [M+] 679.

EXAMPLE 6

Preparation of 3'-deamino-3'-[1-aziridinyl]-4'-deoxydoxorubicin (2h: $R_1$=OCH$_3$, $R_2$=OH, $R_3$=$R_4$=H).

3'-N-(2-chloroethyl)-4'-deoxydoxorubicin (6c: $R_1$=OCH$_3$, $R_2$=OH, $R_9$=Cl, $R_3$=$R_4$=H), prepared as described in GB 9114549, is converted into the title compound 2h as described in Example 1. TLC on Kieselgel Plates F254 (Merck), using the eluting system methylene chloride and acetone (20:1 by volume) Rf=0.33. FD-MS: m/z [M+] 553.

BIOLOGICAL ACTIVITY

3'-deamino-3'-[1-aziridinyl]-4'-O-methansulfonyl daunorubicin (1a), 4-demethoxy-3'-deamino-3'-[1-aziridinyl]-4'-O-methansulfonyl daunorubicin (1b), 3'-deamino-3'-[1-aziridinyl]-4'-O-methansulfonyl-14-nicotinate-doxorubicin (2a) and 3'-deamino-3'-[1-aziridinyl]-4'-O-methansulfonyl doxorubicin (2c), were tested in vitro on two human cell lines, LoVo (colon adenocarcinoma) and LoVo/DX (colon adenocarcinoma resistant to doxorubicin) in comparison with doxorubicin.

The citotoxic activity is reported as IC50, the concentration inhibiting 50% of colony formation, calculated on concentration response curves. Resistance index R.I. is the ratio between the IC50 on resistant cells and the IC50 on sensitive cells. Compounds 1a, 1b, 2a and 2c showed high activity against both cell lines and had a low resistance index (Table I).

Compounds 1a, 1b, 2a and 2c were also evaluated in vivo against P388 murine leukaemia resistant to doxorubicin ($10^5$ cell/mouse transplanted i.v. in BD2F1 mice) in comparison with doxorubicin.

Compounds 1a, 1b, 2a and 2c also showed strikingly higher activity than doxorubicin (Table II).

TABLE 1 in vitro cytotoxic activity (IC50) of compounds 1a, 1b, 2a and 2c on LoVo and LoVo/DX cells in comparison with doxorubicin.

| compound | IC$_{50}$ (ng/ml)[1] | | |
|---|---|---|---|
| | LoVo | LoVo/DX | R.I.[2] |
| 1a | 13 | 22 | 1.7 |
| 1b | 27 | 26 | 0.9 |
| 2a | 14 | 40 | 2.9 |
| 2c | 2.7 | 24 | 9.2 |
| doxorubicin | 82.5 | 4975 | 60.3 |

Colony assay: 4 h treatment
[1]IC$_{50}$ = concentration inhibiting 50% colony formation
[2]R.I. = Resistance Index = (IC50 LoVo/DX)/(IC50 LoVo)

TABLE 2

Antitumor activity of compounds 1a, 1b, 2a and 2c on P388/DX leukaemia in comparison with doxorubicin.

| compound | O.D.[1] (mg/kg) | T/C[2] % |
|---|---|---|
| 1a | 2.2 | 190 |
| 1b | 3.8 | 240 |
| 2a | 2.5 | 200 |
| 2c | 1.8 | 195 |
| doxorubicin | 16.9 | 106 |

The compounds were suspended in Tween 80 (10%) and injected i.v. one day after tumor transplantation.
[1]Optimal Dose
[2]Median survival time of treated mice/Median survival time of controls × 100.

We claim:
1. A compound which is an anthracycline glycoside of formula (1) or (2):

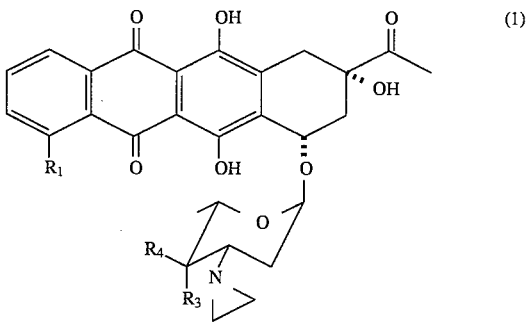

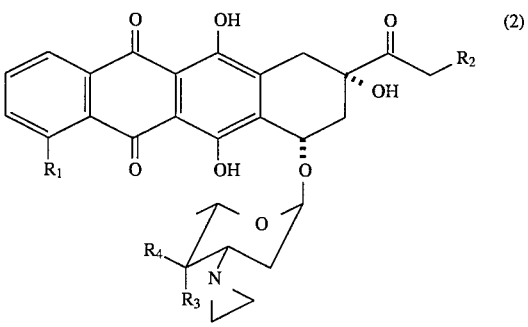

wherein $R_1$ is hydrogen or methoxy; $R_2$ is hydrogen, hydroxy or represents an acyloxy residue of formula 3:

$$—O—COR_5 \qquad (3)$$

wherein $R_5$ is a linear or branched $C_1$–$C_8$ alkyl, a mono- or bicyclic aryl group of 6 to 10 carbon atoms or a 5- or 6-membered saturated or unsaturated heterocyclic ring containing at least one heteratom selected from the group consisting of O, S and N, and which is optionally fused to a second 5- or 6-membered, saturated or unsaturated heterocyclic group as defined above; said mono- or bicyclic aryl group or said heterocyclyl ring or rings each being unsubstituted or substituted with:
   (a) an amino group —NR$_6$R$_7$, in which R$_6$ and R$_7$ are each independently hydrogen or $C_1$–$C_4$ alkyl, or,
   (b) a carboxy group;

$R_3$ and $R_4$ both represent hydrogen or one of $R_3$ and $R_4$ is hydrogen and the other is a hydroxy group or a group of the formula —OSO$_2$R$_8$, in which $R_8$ is a linear or branched alkyl group containing from 1 to 6 carbon atoms or an aryl group which is unsubstituted or substituted by one to three substituents each of which is independently a linear or branched alkyl or alkoxy group of from 1 to 6 carbon atoms, halogen or nitro; or a pharmaceutically acceptable salt thereof.

2. The compound of claim 1, wherein $R_5$ is phenyl.
3. The compound of claim 1, wherein $R_5$ is pyridyl.
4. The compound of claim 1, wherein $R_8$ is methyl, ethyl, n-propyl or isopropyl.
5. The compound of claim 1, wherein $R_8$ is unsubstituted phenyl or phenyl substituted by 1 to 3 substituents, each of which is independently a linear or branched alkyl or alkoxy group of from 1 to 3 carbon atoms.
6. The compound of claim 1, which is:

3'-deamino-3'-(1-aziridinyl)-4'-O-methanesulfonyl daunorubicin;

4-demethoxy-3'-deamino-3'-(1-aziridinyl)-4'-O-methanesulfonyl daunorubicin;

3'-deamino-3'-(1-aziridinyl)-daunorubicin;

4-demethoxy-3'-deamino-3'-(1-aziridinyl)-daunorubicin;

3'-deamino-3'-(1-aziridinyl)-4'-O-methanesulfonyl-14-nicotinate-doxorubicin;

3'-deamino-3'-(1-aziridinyl)-14-nicotinate-doxorubicin;

3'-deamino-3'-(1-aziridinyl)-4'-O-methanesulfonyl doxorubicin;

4-demethoxy-3'-deamino-3'-(1-aziridinyl)-4'-O-methanesulfonyl doxorubicin;

3'-deamino-3'-(1-aziridinyl)-doxorubicin;

4-demethoxy-3'-deamino-3'-(1-aziridinyl)-doxorubicin;

3'-deamino-3'-(1-aziridinyl)-4'-iododoxorubicin; or

3'-deamino-3'-(1-aziridinyl)-4'-deoxydoxorubicin.

7. The compound of claim 1, which is:

3'-deamino-3'-(1-aziridinyl)-4'-O-methanesulfonyl daunorubicin;

4-demethoxy-3'-deamino-3'-(1-aziridinyl)-4'-O-methanesulfonyl daunorubicin; or

3'-deamino-3'-(1-aziridinyl)-4'-O-methansulfonyl-14-nicotinate-doxorubicin.

8. The compound of any one of claims 1–7, which is in the form of a hydrochloride salt.

9. A pharmaceutical composition comprising a pharmaceutically acceptable diluent or carrier and, as an active component, one or more of the anthracycline glycosides of claim 1.

10. A method for treating a tumor in a human or animal body, which comprises administering to a human or animal in need thereof an effective amount of one or more anthracycline glycosides or a pharmaceutically acceptable salt thereof as defined in claim 1.

* * * * *